(12) United States Patent
Khosravani

(10) Patent No.: US 10,317,353 B2
(45) Date of Patent: Jun. 11, 2019

(54) METHOD AND SYSTEM FOR NON-DESTRUCTIVE TESTING

(71) Applicant: THE BOEING COMPANY, Chicago, IL (US)

(72) Inventor: Shahriar Khosravani, Everett, WA (US)

(73) Assignee: THE BOEING COMPANY, Chicago, IL (US)

( * ) Notice: Subject to any disclaimer, the term of this patent is extended or adjusted under 35 U.S.C. 154(b) by 0 days.

(21) Appl. No.: 15/464,204

(22) Filed: Mar. 20, 2017

(65) Prior Publication Data

US 2018/0266974 A1    Sep. 20, 2018

(51) Int. Cl.
| | |
|---|---|
| G01R 31/12 | (2006.01) |
| G01N 27/04 | (2006.01) |
| G01R 27/08 | (2006.01) |
| G01R 27/14 | (2006.01) |
| H02G 13/00 | (2006.01) |

(52) U.S. Cl.
CPC ......... *G01N 27/041* (2013.01); *G01R 27/08* (2013.01); *G01R 27/14* (2013.01); *G01R 31/1227* (2013.01); *H02G 13/60* (2013.01)

(58) Field of Classification Search
USPC .......................................... 324/693; 702/182
See application file for complete search history.

(56) References Cited

U.S. PATENT DOCUMENTS

| | | | |
|---|---|---|---|
| 9,276,391 B2 | 3/2016 | Hasenoehrl et al. | |
| 9,488,609 B2 | 11/2016 | Khosravani | |
| 2008/0307886 A1* | 12/2008 | Marsh ................... | G01N 29/223 |
| | | | 73/601 |

(Continued)

FOREIGN PATENT DOCUMENTS

| | | |
|---|---|---|
| CN | 105158572 A * | 12/2015 |
| EP | 2905610 A1 | 8/2015 |
| WO | 2011131995 A1 | 10/2011 |

OTHER PUBLICATIONS

Duan et al., Lightning Direct Effect Experimental Research on Rotor Blade of a Helicopter, 2015.*

(Continued)

*Primary Examiner* — Patrick Assouad
*Assistant Examiner* — Demetrius R Pretlow
(74) *Attorney, Agent, or Firm* — Toler Law Group, P.C.

(57) ABSTRACT

A non-destructive testing system includes a test article interface and a reference article interface. The test article interface includes a connector to couple to a metal component of an article under test (AUT) and a connector to couple to a carbon fiber composite component of the AUT. The reference article interface includes a connector to couple to a metal component of a reference article (REF) and a connector to couple to a carbon fiber composite component of the REF. The system also includes sensors to generate signals based on voltage and current thermoelectrically induced between the test article interface and the reference article interface, where the current and the voltage are based on a temperature difference between the AUT and the REF. The system also includes a processor to generate, based on the signals, an output indicating whether the AUT is expected to pass a lightning strike test.

20 Claims, 5 Drawing Sheets

(56) References Cited

U.S. PATENT DOCUMENTS

| | | | |
|---|---|---|---|
| 2010/0010794 A1* | 1/2010 | Sweers | G06F 17/5009 |
| | | | 703/8 |
| 2010/0215358 A1 | 8/2010 | Harres et al. | |
| 2011/0014356 A1* | 1/2011 | Fornes | C09D 7/62 |
| | | | 427/58 |
| 2012/0119761 A1 | 5/2012 | Pons et al. | |
| 2015/0212136 A1* | 7/2015 | Iwaki | B64D 45/02 |
| | | | 702/58 |
| 2015/0219577 A1* | 8/2015 | Khosravani | G01N 27/20 |
| | | | 324/693 |
| 2016/0018459 A1* | 1/2016 | Ohtsuka | G01R 31/025 |
| | | | 324/754.21 |
| 2016/0297542 A1 | 10/2016 | Khosravani et al. | |
| 2016/0369781 A1* | 12/2016 | March Nomen | F03D 1/0675 |
| 2018/0074036 A1* | 3/2018 | Boettcher | G01N 33/227 |

OTHER PUBLICATIONS

Advisory Circular, "Protection of Aircraft Electrical/Electronic Systems Against the Indirect Effects of Lightning," US Department of Transportation, Federal Aviation Administration, Dec. 21, 2006, AC No. 20-136A, 29 pgs.

Rupke, Ed, "Lightning Direct Effects Handbook," AGATE—Advanced General Aviation Transportation Experiments, Mar. 1, 2002, Report Reference No. AGATE-WP3.1-031027-043-Design Guideline Work Package Title: WBS3.0 Integrated Design and Manufacturing, 119 pgs.

Extended European Search Report for Application No. 18151915.8 dated Jul. 30, 2018, 11 pgs.

Evans, Simon et al., "Lightning Strike Protection of Aircraft Structural Joints," 2014 International Conference on Lightning Protection (ICLP), Shanghai, China, 2014, pp. 1952-1959.

\* cited by examiner

METHOD AND SYSTEM FOR NON-DESTRUCTIVE TESTING

FIELD

The present disclosure generally relates to non-destructive testing.

BACKGROUND

The effects of inclement weather conditions may significantly influence design decisions for structures or systems exposed to the environment. For example, particular materials or a particular arrangement of components may be selected based on environmental conditions to which a structure or system may be exposed. Further, the particular materials or the particular arrangements of components may be subjected to testing to confirm the design decision.

One specific example of a test for operation in specific environmental conditions is direct lightning effect testing. Direct lightning effect testing subjects a system or a component to high current pulses to understand the effect of such high current pulses on materials of the system or the component. For example, an aircraft may be required to pass a direct lightning effect test standard before the aircraft is certified for operation by a governmental entity, such as the U.S. Federal Aviation Administration. Other systems may also be subjected to direct lightning effect testing, such wind turbines, architectural features, etc.

Performing a direct lightning effect test can be quite resource intensive. For example, large banks of capacitors and complex switching and control systems are generally used to generate the short duration, high current pulses. Also, direct lightning effect tests are destructive tests in that parts subjected to direct lightning effect testing are not generally immediately reusable. For example, the part may be damaged in a manner that requires inspection or repair before use.

SUMMARY

In a particular example, a non-destructive testing system includes a test article interface and a reference article interface. The test article interface includes a first electrical connector configured to couple to a metal component of an article under test and a second electrical connector configured to couple to a carbon fiber composite component of the article under test. The reference article interface includes a third electrical connector configured to couple to a metal component of a reference article and a fourth electrical connector configured to couple to a carbon fiber composite component of the reference article. The non-destructive testing system also includes at least one sensor electrically connected to the test article interface and electrically connected to the reference article interface. The at least one sensor is configured to generate at least one signal based on a voltage between the test article interface and the reference article interface and based on a current between the test article interface and the reference article interface, where the current and the voltage are based on a temperature difference between the article under test and the reference article. The non-destructive testing system further includes a processor configured to generate, based on the at least one signal from the at least one sensor, an output indicating whether the article under test is expected to satisfy a lightning test standard.

In another particular example, a method includes determining, at a non-destructive testing system, whether a temperature difference between an article under test and a reference article satisfies a temperature criterion, where the article under test includes a carbon fiber composite component and a metal component. The method also includes, based on a determination that the temperature difference satisfies the temperature criterion, sensing, by the non-destructive testing system, a thermoelectrically induced voltage between the article under test and the reference article and sensing, by the non-destructive testing system, a thermoelectrically induced current between the article under test and the reference article. The method further includes generating, by the non-destructive testing system based on the thermoelectrically induced voltage and the thermoelectrically induced current, an output indicating whether the article under test is expected to satisfy a lightning test standard.

In another particular example, a computer readable storage device stores instructions that, when executed by a processor of a non-destructive testing system, cause the processor of the non-destructive testing system to perform operations. The operations include determining whether a temperature difference between an article under test and a reference article satisfies a temperature criterion. The operations also include, based on a determination that the temperature difference satisfies the temperature criterion, determining an effective resistance of the article under test based on a thermoelectrically induced voltage between the article under test and the reference article and based on a thermoelectrically induced current between the article under test and the reference article. The operations further include generating an output indicating whether the article under test is expected to satisfy a lightning test standard.

The described features, functions, and advantages may be achieved independently in various embodiments or may be combined in yet other embodiments further details of which can be seen with reference to the following description and drawings.

DETAILED DESCRIPTION

Figure 1:
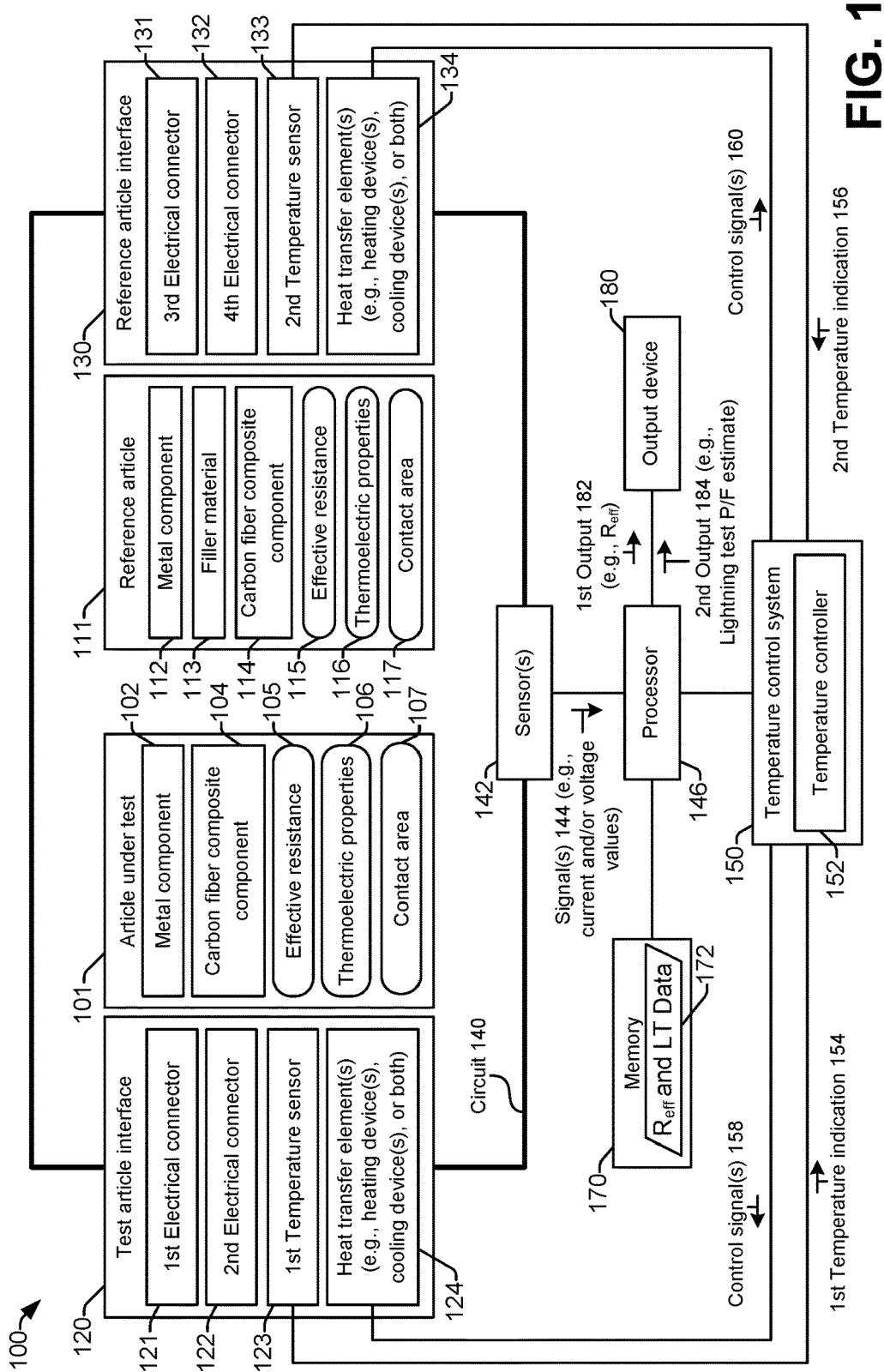
FIG. 1 is a block diagram of a particular embodiment of a non-destructive testing system.

The present disclosure describes a system and method for non-destructive testing. The non-destructive testing of a component is performed in a manner that is compatible with subsequent performance of a direct lightning effect test on the same component. For example, the non-destructive testing is thermodynamically reversible, and does not subject the component to any external influence (such as an external current or voltage) that would potentially change the outcome of the direct lightning effect test. Thus, an article under test (e.g., a test coupon) can be subjected to non-destructive testing and can subsequently be used to demonstrate compliance with a direct lightning effect test standard. Further, the non-destructive testing can be used to predict whether the article under test is likely to pass (e.g., comply with requirements of or satisfy a standard related to) the direct lightning effect test. Thus, if the article under test performs adequately on the non-destructive testing, the article under test can be subjected to the more expensive and resource intensive direct lightning effect test. However, if the article under test does not perform adequately on the non-destructive testing, the time and expense of the subjecting the article under test to the direct lightning effect test can be avoided since the article under test is not expected to pass the direct lightning effect test.

The non-destructive testing disclosed herein can be used to test articles formed of two or more different materials, such as an article that includes an interface between a composite material and a metal. Interfaces between metallic and semi-metallic materials having different thermoelectric properties can generate an electromotive force due, for example, to the Seebeck effect. Thus, if the composite material includes metallic and semi-metallic components, such as carbon fibers, the interface between the metallic and semi-metallic components and the metal portion can thermoelectrically induce a current, a voltage, or both.

By measuring a thermoelectrically induced current and a thermoelectrically induced voltage, an effective resistance of a circuit including the article under test can be determined. The effective resistance provides an indication of whether the article under test is likely to pass a direct lightning effect test. For example, the effective resistance (or another value determined based on the effective resistance) can be compared to the lightning test data of articles that have been subjected to a direct lightning effect test to determine whether the article under test is likely to pass the direct lightning effect test. As another example, the effective resistance of articles that passed the direct lightning effect test and the effective resistance of articles that did not pass the direct lightning effect test can be used to determine a threshold effective resistance to model direct lightning effect test outcomes (e.g., using a support vector machine model or another non-linear classifier). In this example, the effective resistance of the circuit including the article under test may be compared to the model of the direct lightning effect test outcomes to predict, based on the non-destructive test, whether the article under test is expected to pass the direct lightning effect test.

Large, complex systems, such as aircraft and wind turbines, may have many material interfaces that could be effected differently by the direct lightning effect test. Using the non-destructive test described herein may enable a designer or manufacturer to limit use of direct lightning effect testing to systems or components that have a high likelihood of passing the direct lightning effect test standard.

Further, design changes or manufacturing process changes may merit retesting of particular components. For example, the effective resistance of a component may be a function of many factors, such as types of materials used, contact area between different materials (e.g., metal and composite) used, and orientations of different anisotropic materials used. As a specific example, changing the size, shape, or orientation of a metal connector coupled to a carbon fiber composite can change the effect resistance of the interface between the carbon fiber composite and the metal connector, which may change the outcome of the direct lightning effect test. Other changes can also change the effective resistance. To illustrate, changing a manufacturing technique used to prepare a hole in the carbon fiber composite to receive the metal connector can change the contact area between the metal connector and the carbon fiber composite. As another illustrative example, the contact area between the metal connector and the carbon fiber composite can be changed by addition of another material, such as a lubricant or an adhesive, between the carbon fiber composite and the metal connector. If many such design changes or manufacturing process changes are encountered, the savings associated with using the non-destructive testing described herein as a "pretest" to determine whether to subject an article to the direct lightning effect test can be significant.

The non-destructive test disclosed herein uses measurements of a thermoelectrically induced voltage and a thermoelectrically induced current between an article under test and a reference article to determine an effective resistance of a circuit including the article under test. The article under test may have a specific configuration of materials formed using a specific manufacturing process that is to be tested for compliance with a direct lightning effect test. The reference article is substantially a duplicate of the article under test (e.g., includes the specific configuration of materials formed using the specific manufacturing process); however, the reference article includes a filler material that decreases the effective resistance of the reference article by increasing an effective contact area between materials of the reference article.

To perform the non-destructive test, the article under test and the reference article are electrical connected to one another and to one or more sensors. A temperature of the article under test, a temperature of the reference article, or both, is controlled to establish a particular temperature difference between the article under test and the reference article. The temperature difference and the thermoelectric properties of the materials involved induce (e.g., by the Seebeck effect) a current, a voltage, or both, between the article under test and the reference article. Since the article under test is not subjected to external forces or effects that would potentially alter the outcome of the direct lightning effect test, the article under test can be subjected to a direct lightning effect test after the non-destructive test is performed. Further, since the non-destructive test can be used to predict whether the article under test is likely to pass the direct lightning effect test standard, the article under test may not be subject to the direct lightning effect test if the non-destructive test indicates that the article under test is not likely to pass the direct lightning effect test standard.

Figure 2:
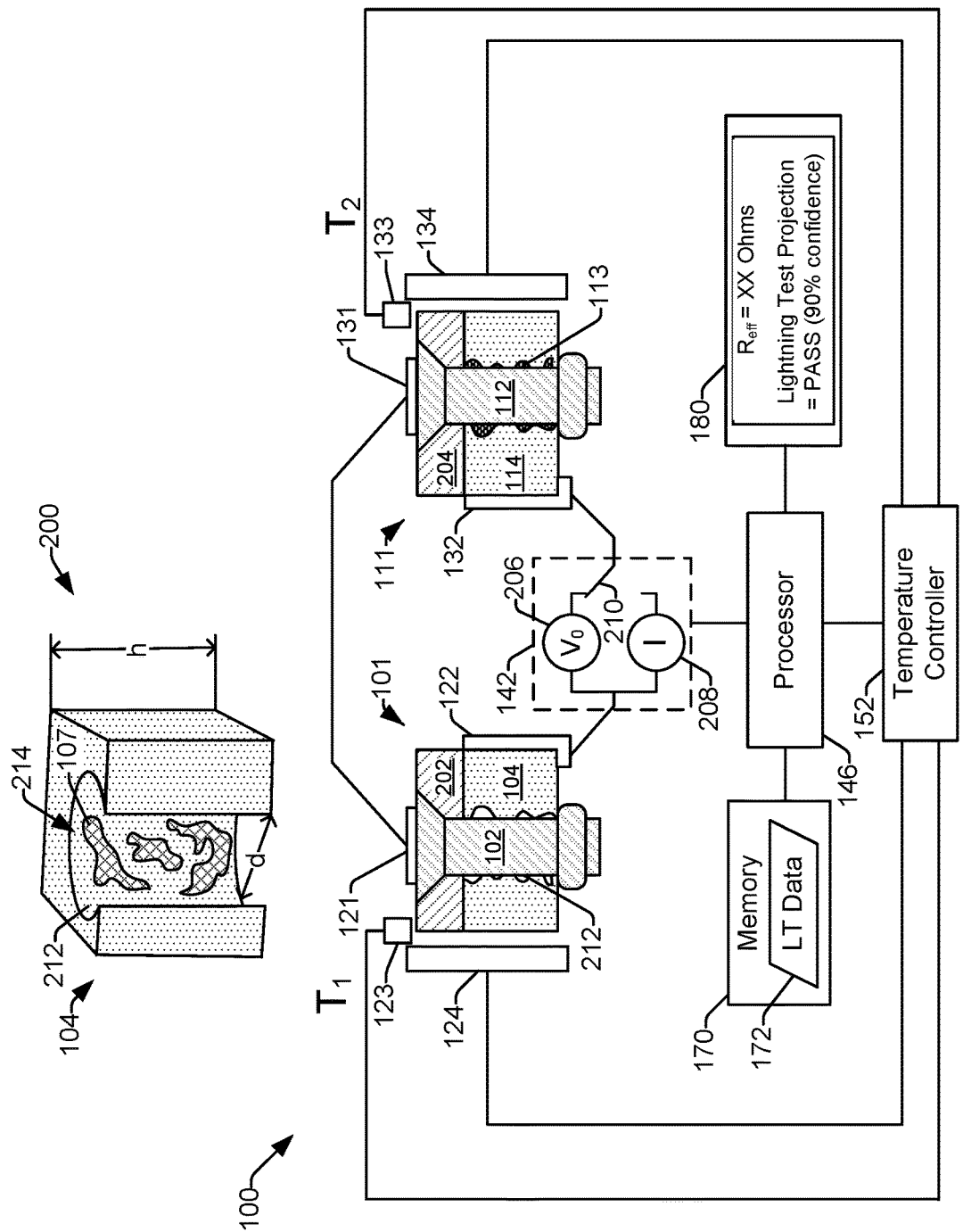
FIG. 2 is diagram depicting a particular example of the non-destructive testing system of FIG. 1.

FIG. 1 is a block diagram of a particular embodiment of a non-destructive testing system. The non-destructive testing system 100 includes a test article interface 120 and a reference article interface 130. Although the test article interface 120 and the reference article interface 130 are each illustrated in FIG. 1 by a representative block, the test article interface 120 and the reference article interface 130 may correspond to or include multiple discrete and physically disconnected components, as illustrated in FIG. 2.

The test article interface 120 includes a first electrical connector 121 configured to couple to a metal component 102 of an article under test 101 and a second electrical connector 122 configured to couple to a carbon fiber composite component 104 of the article under test 101. The first electrical connector 121 couples to a portion of the metal component 102 of the article under test 101 and the second electrical connector 122 couples to a portion of the carbon fiber composite component 104 of the article under test 101 such that a current path is provided between the first electrical connector 121 and the second electrical connector 122. For example, the metal component 102 of the article under test 101 contacts one or more carbon fibers of the carbon fiber composite component 104 of the article under test 101. The current path allows current to flow from the first electrical connector 121 to the metal component 102 of the article under test 101, from the metal component 102 of the article under test 101 to the one or more carbon fibers of the carbon fiber composite component 104 of the article under test 101, and from the one or more carbon fibers of the carbon fiber composite component 104 of the article under test 101 to the second electrical connector 122.

The reference article interface 130 includes a third electrical connector 131 configured to couple to a metal component 112 of a reference article 111 and a fourth electrical connector 132 configured to couple to a carbon fiber composite component 114 of the reference article 111. The third electrical connector 131 couples to a portion of the metal component 112 of the reference article 111 and the fourth electrical connector 132 couples to a portion of the carbon fiber composite component 114 of the reference article 111 such that a current path is provided between the third electrical connector 131 and the fourth electrical connector 132. For example, the metal component 112 of the reference article 111 contacts a filler material 113, one or more carbon fibers of the carbon fiber composite component 114 of the reference article 111, or both. The current path allows current to flow from the third electrical connector 131 to the metal component 112 of the reference article 111, from the metal component 112 of the reference article 111 to the one or more carbon fibers of the carbon fiber composite component 114 of the reference article 111 (directly or via the filler material 113), and from the one or more carbon fibers of the carbon fiber composite component 114 of the reference article 111 to the fourth electrical connector 132.

The reference article 111 is substantially a duplicate of the article under test (except for the filler material 113 of the reference article 111). For example, the carbon fiber composite component 104 of the article under test 101 and the carbon fiber composite component 114 of the reference article 111 are formed of a same type of composite material. Likewise, the metal component 102 of the article under test 101 and the metal component 112 of the reference article 111 are a same type of connector.

The filler material 113 between the metal component 112 of the reference article 111 and the carbon fiber composite component 114 of the reference article 111 is configured to decrease an effective resistance 115 of the reference article 111 relative to the effective resistance 105 of the article under test 101. The effective resistance 105 of the article under test 101 is indicative of a contact area 107 between the carbon fiber composite component 104 of the article under test 101 and the metal component 102 of the article under test 101. The filler material 113 increase a contact area 117 between the carbon fiber composite component 114 of the reference article 111 and the metal component 112 of the reference article 111 relative to the contact area 107 of the article under test 101. The increased contact area 117 of the reference article 111 decreases the effective resistance of the reference article 111 relative to the article under test 101.

For example, in a particular configuration, the article under test 101 and the reference article 111 are test specimens that each include a metal fastener extending through a hole in a carbon fiber composite test coupon. In this example, when the hole is formed in the carbon fiber composite test coupon, some of the carbon fibers of the carbon fiber composite may be cut and exposed within the hole or at edges of the hole. When the metal fastener is inserted into the hole, the metal fastener intersects (e.g., comes into electrical contact with) at least a subset of the exposed carbon fibers. The portions of the metal fastener that contact the exposed carbon fibers define the contact area of the test specimen. For example, the contact area 107 of the article under test 101 is based on how much of the metal component 102 is in contact with carbon fibers of the carbon fiber composite component 104. Likewise, the contact area 117 of the reference article 111 is based on how much of the metal component 112 is in contact with carbon fibers of the carbon fiber composite component 114. The filler material 113 provides an electrical conduction path between the metal component 112 and exposed carbon fibers of the carbon fiber composite component 114 that are not in direct physical contact with the metal component 112. Thus, the contact area 117 of the reference article 111 is larger than the contact area 107 of the article under test 101.

The non-destructive testing system 100 also includes at least one sensor, e.g., sensor(s) 142, electrically connected to the test article interface 120 and electrically connected to the reference article interface 130. The sensor(s) 142 are configured to generate a signal or signals, e.g., signal(s) 144, based on (e.g., indicating a measurement of) a voltage between the test article interface 120 and the reference article interface 130, a signal based on (e.g., indicating a measurement of) a current between the test article interface 120 and the reference article interface 130, or based on (e.g., indicating measurements of) the current and the voltage.

The current and the voltage are based on a temperature difference between the article under test 101 and the reference article 111. For example, the voltage and the current may be induced by the temperature difference and thermoelectric properties 106, 116 of materials of the article under test 101 and the reference article 111 as a result of the Seebeck effect.

The non-destructive testing system 100 may include a temperature control system 150 configured to control the temperature difference between the article under test 101 and the reference article 111. In a particular example, the temperature control system 150 includes a temperature controller 152 coupled to multiple temperature sensors, such as a first temperature sensor 123 coupled to the test article interface 120 and a second temperature sensor 133 coupled to the reference article interface 130. The temperature control system 150 is coupled to at least one heat transfer element 124, 134. For example, the at least one heat transfer element 124, 134 may include at least one heating device coupled to the test article interface 120 and at least one cooling device coupled to the reference article interface 130. As another example, the at least one heat transfer element 124, 134 may include at least one cooling device coupled to the test article interface 120 and at least one heating device coupled to the reference article interface 130. In still other examples, the at least one heat transfer element 124, 134 includes other combinations of heating devices and cooling devices coupled to the test article interface 120 and the reference article interface 130.

The temperature controller 152 is configured to receive a first temperature indication 154 from the first temperature sensor 123, to receive a second temperature indication 156 from the second temperature sensor 133, and to provide control signals 158, 160 to the at least one heat transfer element 124, 134 to control the temperature difference between the article under test 101 and the reference article 111. The control signals 158, 160 are based the first temperature indication 154 and the second temperature indication 156.

The non-destructive testing system 100 also includes a processor 146 configured to generate, based on the signal(s) 144 from the sensor(s) 142, an output 182. The output 182 includes data representative of an effective resistance 105 of the article under test 101. For example, the output 182 may indicate a value of the effective resistance 105. As another example, the output 182 may indicate a value of a total resistance of a circuit 140 including the article under test 101. As yet another example, the output 182 may indicate whether the effective resistance 105 (or the total resistance of the circuit 140) satisfies a criterion, such as whether the effective resistance 105 (or the total resistance of the circuit 140) is greater than or less than a particular threshold value, such as an effective resistance (or total resistance) associated with passing a direct lighting effect test standard.

During operation, the test article interface 120 and the reference article interface 130 are electrically interconnected to form the circuit 140. The circuit 140 electrically connects a first portion of the article under test 101 and a second portion of the reference article 111 and electrically connects the at least one sensor 142 to a third portion of the article under test 101 and to a fourth portion of the reference article 111. For example, as illustrated in FIG. 2, the metal component 102 of the article under test 101 may be electrical connected to the metal component 112 of the reference article 111, and the carbon fiber composite component 104 of the article under test 101 may be electrically connected (via the sensor(s) 142) to the carbon fiber composite component 114 of the reference article 111.

When the temperature control system 150 indicates that the temperature difference fails to satisfy the temperature criterion, the temperature controller 152 sends control signals 158, 160 to the heat transfer element(s) 124, 134 to adjust the temperature of the article under test 101, the temperature of the reference article 111, or both. For example, based on the temperature difference, the temperature controller 152 sends control signal(s) 158, 160 to heat to the article under test 101, to cool (i.e., remove heat from) the article under test 101, to heat the reference article 111, to cool the reference article 111, or a combination thereof.

When the temperature control system 150 determines that the temperature difference satisfies the temperature criterion, the temperature control system 150 may send a signal to the processor 146. The processor 146 generates an estimate of the effective resistance 105 of the article under test 101 (or of the circuit 140) based on the indication that the temperature difference satisfies the temperature criterion. The effective resistance of the circuit 140 is calculated (e.g., using Ohm's law) based on the thermoelectrically induced voltage between the article under test 101 and the reference article 111 and the thermoelectrically induced current between the article under test 101 and the reference article 111. The effective resistance 105 of the article under test 101 can be calculated (or estimated) by subtracting an effective resistance 115 of the reference article 111 from the effective resistance of the circuit 140. Since the reference article 111 will not be used for direct lightning effect testing, the effective resistance 115 of the reference article 111 can be determined by other testing, such as applying a known voltage from an external source to the reference article 111 and measuring the resulting current.

After the effective resistance of the article under test 101 or of the circuit 140 is determined, the processor 146 performs a comparison of the effective resistance to lightning test data 172 for articles subjected to a destructive lightning strike test to generate an output 184 indicating whether the article under test 101 is expected to pass the destructive lightning strike test. In some implementations, the processor 146 compares a different value to the lightning test data 172. For example, the processor 146 may determine the contact area 107 (as described further below) of the article under test 101 and compare the contact area 107 to the lightning test data 172 to generate the output 184 indicating whether the article under test 101 is expected to pass the destructive lightning strike test. To illustrate, the lightning test data 172 may be evaluated to determine a threshold contact area (for particular materials or for a particular arrangement of material) that is associated with passing the destructive lightning strike test, and the contact area 107 of the article under test 101 may be compared to the threshold contact area to determine whether the article under test 101 is likely to pass the destructive lightning strike test. Thus, the non-destructive testing system 100 enables non-destructive testing of the article under test 101 to estimate or predict whether the article under test 101 is likely to pass a destructive lightning strike test, such as a direct lightning effect test.

FIG. 2 is diagram depicting particular example of non-destructive testing system 100 of FIG. 1. The diagram of FIG. 2 illustrates one particular example of a physical arrangement of the article under test 101, the reference article 111, the test article interface 120, the reference article interface 130, and the sensor(s) 142 of FIG. 1. The diagram of FIG. 2 also illustrates a perspective sectional view 200 of the carbon fiber composite component 104.

In FIG. 2, the carbon fiber composite component 104 of the article under test 101 is coupled to a layer 202 by the metal component 102. Likewise, the carbon fiber composite component 114 of the reference article 111 is coupled to a layer 204 by the metal component 112. In FIG. 2, the metal components 102, 112 include fasteners, such as bolts, rivets, screws, pins, studs, staples, or other fasteners formed of or including metal. In other examples, the metal components 102, 112 corresponds to the layer 202, 204. To illustrate, the layer 202 may be formed of or include metal (e.g., a metal panel) that is coupled to the carbon fiber composite component 104 in a manner that allows electrical contact between the layer 202 and carbon fibers of the carbon fiber composite component 104. In other examples, the layers 202, 204 are omitted from the article under test 101 and the reference article 111.

As shown in the perspective sectional view 200, the carbon fiber composite component 104 includes (e.g., defines) an opening 214 to receive the metal component 102. The opening 214 defines an available contact area between the carbon fiber composite component 104 and the metal component 102. For example, in FIG. 2, the opening 214 is round and has a diameter (d) and a height (h). Thus, the total available contact area between the carbon fiber composite component 104 and the metal component 102 corresponds to a surface area of sidewalls 212 of the opening 214, which is equal to $\pi*d*h$ in FIG. 2. In other examples, the opening 214 may have a different size or shape, and therefore a different surface area of the sidewalls 212. Thus, the example of a circular opening 214 is only one possibility.

Due to irregularities in the sidewalls 212, irregularities in the metal component 102, or other characteristics of the carbon fiber composite component 104 and the metal component 102, the metal component 102 may only contact a portion of the sidewalls 212. In FIG. 2, the portion of the sidewalls 212 contacted by the metal component 102 corresponds to the contact area 107 of the carbon fiber composite component 104 and the metal component 102.

The reference article 111 includes the filler material 113, which fills in gaps between the carbon fiber composite component 114 and the metal component 112. Thus, the contact area 117 of the carbon fiber composite component 114 and the metal component 112 of the reference article 111 is substantially equal to (e.g., within manufacturing tolerances of) the total available contact area between the carbon fiber composite component 114 and the metal component 112 (e.g., π*d*h). Thus, the contact area 117 of the reference article 111 may be greater than the contact area 107 of the article under test 101. Since the effective resistance 105, 115 of each of the articles 101, 111 is related to the contact area 107, 117 of the respective article 101, 111, the effective resistance 105 of the article under test 101 may be greater than the effective resistance 115 of the reference article 111. Accordingly, a value of the effective resistance 105 can be used to estimate the contact area 107. As explained above, the effective resistance 105 of the article under test 101 can be determined based on the effective resistance 115 of the reference article and the effective resistance of the circuit 140. The effective resistance ($R_{eff}$) of the circuit 140 can be calculated using Equation 1:

$$R_{eff} = \frac{V_0}{I} \qquad \text{Equation 1}$$

where $V_0$ is the open circuit voltage measured by the voltage sensor 206, and I is the short circuit current measured by the current sensor 208. The effective resistance 105 decreases as the contact area 107 increases (e.g., the effective resistance 105 is inversely proportional to the contact area 107). Further, the reference article 111 is, for purpose of this analysis, substantially identical to the article under test 101 except that the contact area 117 of the reference article 111 is maximized and the effective resistance 115 of the reference article 111 is minimized. That is, the contact area 117 is considered to be equal to the total surface area ($S_T$) of the opening 214, and the effective resistance 115 of the reference article 111 is a minimum resistance ($R_{min}$) associated with full contact between the metal component 112 and the carbon fiber composite component 114 (e.g., based on testing of the reference article 111). Thus, the contact area 107 ($S_{eff}$) of the article under test can be estimated using Equation 2:

$$S_{eff} = \frac{R_{min} * S_T}{R_{eff}} \qquad \text{Equation 2}$$

FIG. 2 also illustrates a switch 210 to enable switching between multiple sensors of the sensor(s) 142. For example, in a first position, the switch 210 electrically connects a voltage sensor 206 to the circuit 140 to measure a voltage (e.g., an open circuit voltage) between the article under test 101 and the reference article 111. In a second position, the switch 210 electrically connects a current sensor 208 to the circuit 140 to measure a current (e.g., a closed loop current) between the article under test 101 and the reference article 111. The sensors 206, 208 provide signals to the processor 146 to determine an effective resistance value of the circuit 140 (including the article under test 101, the reference article 111, and associated electrical connections there between).

As explained above, the processor 146 is configured to generate an output based on the signals provided by the sensors 206, 208. For example, in FIG. 2, the output includes a display at a display device. In FIG. 2, the display includes data representing the effective resistance 105 of the article under test 101 and includes an indication (e.g., "Lighting Test Projection=PASS") of whether the article under test 101 is likely to pass a destructive lightning strike test. In other examples, the output may include data representing the contact area 107 of the article under test 101 instead of or in addition to the data representing the effective resistance 105 of the article under test 101, the indication of whether the article under test 101 is likely to pass a destructive lightning strike test, or both.

The indication of whether the article under test 101 is likely to pass a destructive lightning strike test may be determined based on the effective resistance 105 of the article under test 101 or based on the contact area 107 of the article under test 101, and based on data associated with previously tested articles (e.g., the lighting test (LT) data 172). In FIG. 2, the display also includes data representing a confidence score (e.g., "90% confidence") associated with the indication of whether the article under test 101 is likely to pass a destructive lightning strike test. The confidence score may be calculated based on a statistical comparison of the effective resistance 105 of the article under test 101 (or the contact area 107 of the article under test 101) and the data associated with the previously tested articles (e.g., the LT data 172).

Figure 3:
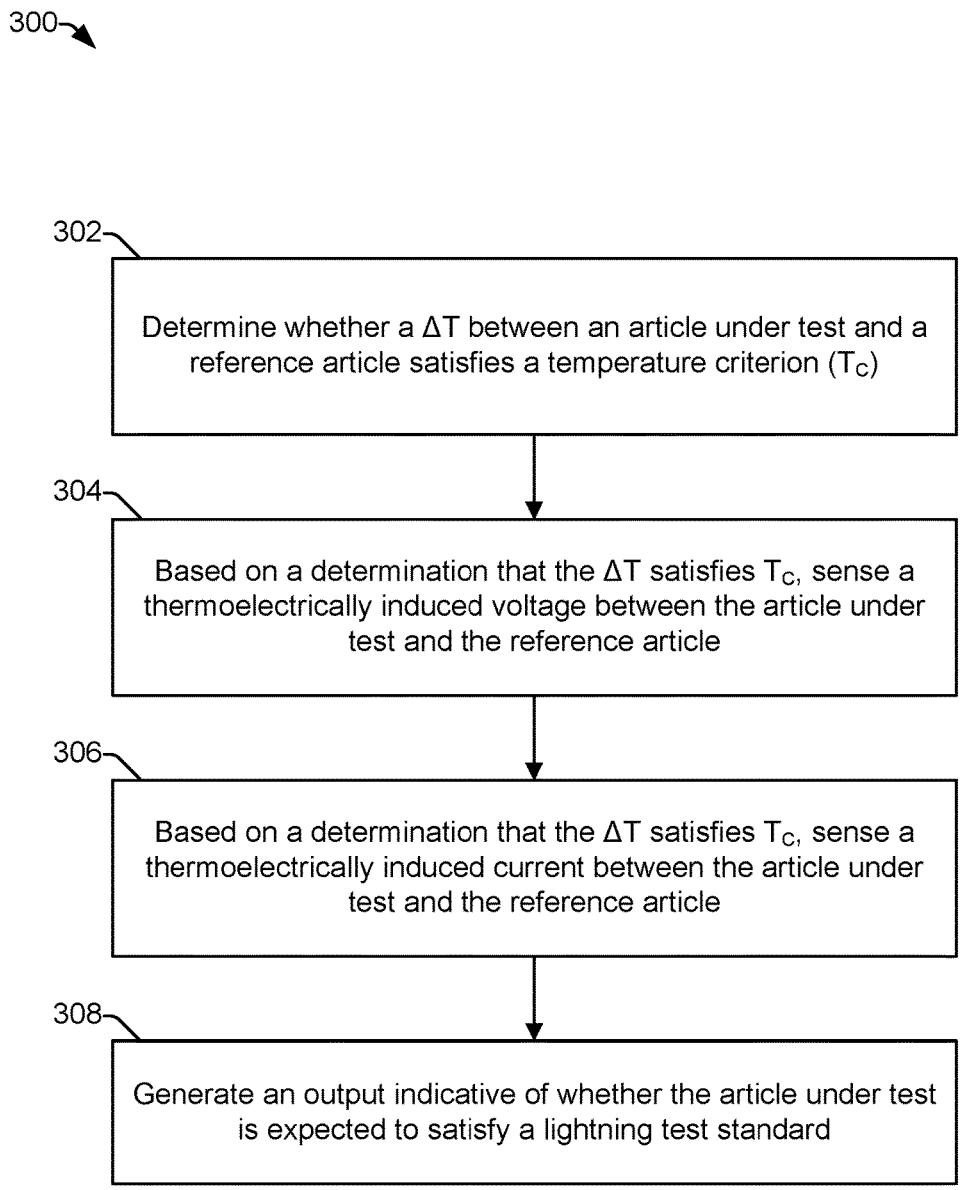
FIG. 3 is a flowchart illustrating a particular example of a method of non-destructive testing.

FIG. 3 a flowchart illustrating an particular example of a method 300 of non-destructive testing. The method 300 may be performed by the non-destructive testing system 100 of FIG. 1 or FIG. 2. For example, the method 300 enables non-destructive testing of an article under test to predict whether the article under test will likely pass a destructive lightning strike test, such as a direct lightning effect test. To perform the method 300, the article under test is coupled to a reference article. The article under test includes a carbon fiber composite component and a metal component. Similarly, the reference article includes a carbon fiber composite component and a metal component. The carbon fiber composite component of the article under test is formed of a particular composite material, and the carbon fiber composite component of the reference article is formed of the particular composite material. Likewise, the metal component of the article under test corresponds to a particular type of connector, and the metal component of the reference article corresponds to the particular type of connector. As described above, the reference article includes a filler material between the metal component of the reference article and the carbon fiber composite component of the reference article. The filler material is configured to decrease an effective resistance of the reference article relative to the effective resistance of the article under test. The effective resistance of the article under test is indicative of a contact area between the carbon fiber composite component of the article under test and the metal component of the article under test.

The method 300 includes, at 302, determining whether a temperature difference between the article under test and the reference article satisfies a temperature criterion. For example, the temperature controller 152 may determine, based on the temperature indications 154, 156 from the temperature sensors 123, 133, whether the temperature difference satisfies the temperature criterion.

The method 300 also includes, at 304, based on a determination that the temperature difference satisfies the temperature criterion, sensing a thermoelectrically induced voltage between the article under test and the reference article. The method 300 also includes, at 306, based on a determination that the temperature difference satisfies the temperature criterion, sensing a thermoelectrically induced current between the article under test and the reference article. For example, the sensors 142 of FIG. 1 may sense the thermoelectrically induced voltage and the thermoelectrically induced current.

The thermoelectrically induced current and voltage tend to be quite small (e.g., in the microvolt and microamp range, respectively), and are related to the temperature difference. The temperature criterion is selected such that the expected thermoelectrically induced current and voltage have a sufficient magnitude for reliable measurement. In some implementations, multiple current and voltage readings may be determined over a range of temperature differences. Taking multiple measurements over a range of temperature differences may reduce errors associated with the voltage and current measurements.

The method 300 also includes, at 308, generating, based on the thermoelectrically induced voltage and the thermoelectrically induced current, an output indicating whether the article under test is likely to pass the destructive lightning strike test (e.g., is expected to satisfy a lightning test standard). The output may also, or in the alternative, include an indication of an effective resistance of the article under test, a contact area of the article under test, or both. As another example, the output may indicate whether the effective resistance of the article under test or the contact area of the article under test satisfies a criterion, such as a criterion indicating whether the article under test is expected to pass the destructive lightning strike test.

Figure 4:
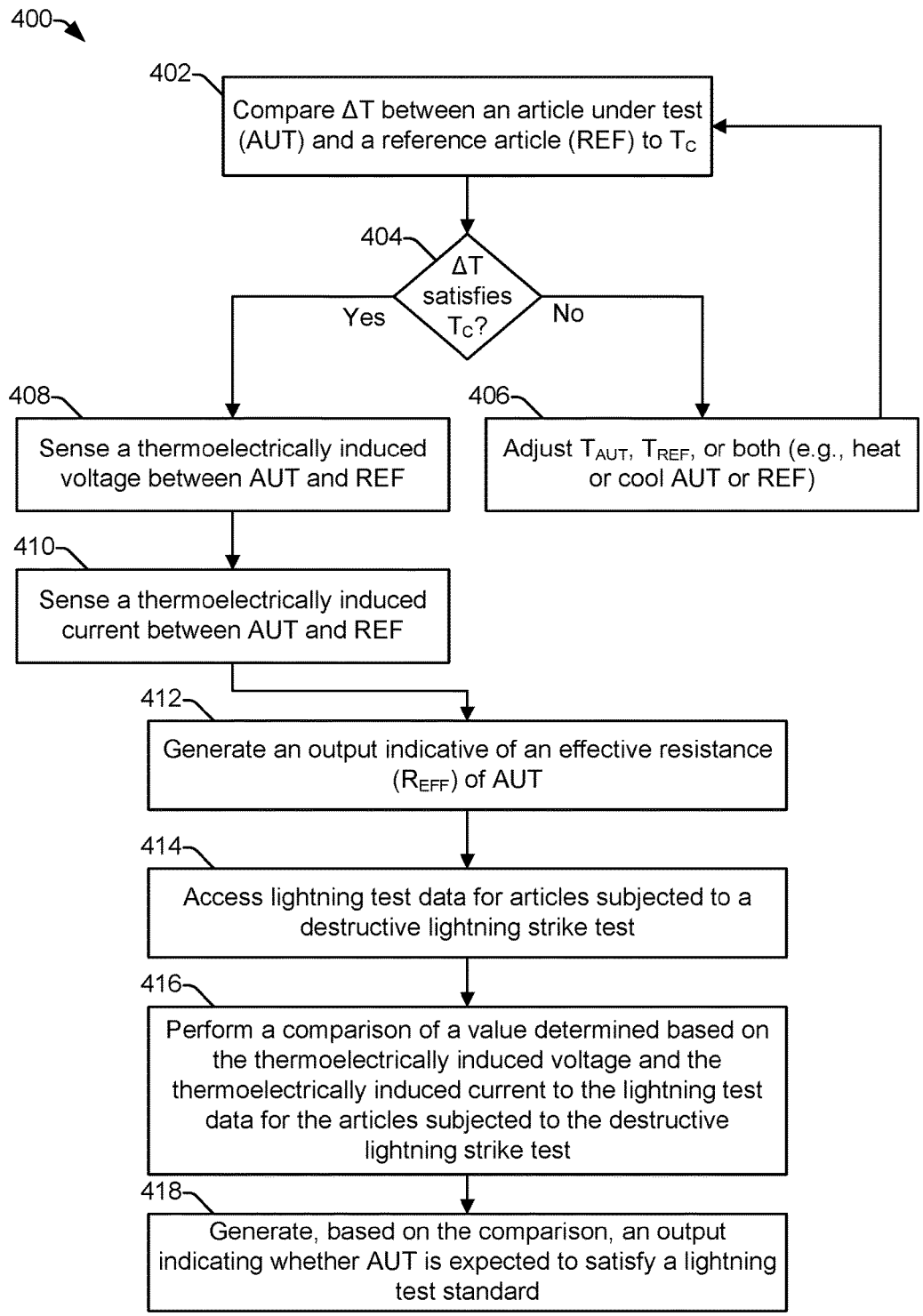
FIG. 4 is a flowchart illustrating another particular example of a method of non-destructive testing.

FIG. 4 a flowchart illustrating a more detailed example of a method of non-destructive testing. The method 400 may be performed by the non-destructive testing system 100 of FIG. 1 or FIG. 2. The method 400 enables non-destructive testing of an article under test to predict whether the article under test will likely pass a destructive lightning strike test, such as a direct lightning effect test.

To perform the method 400, the article under test is coupled to a reference article. The article under test includes a carbon fiber composite component and a metal component. Similarly, the reference article includes a carbon fiber composite component and a metal component. The carbon fiber composite component of the article under test is formed of a particular composite material, and the carbon fiber composite component of the reference article is formed of the particular composite material. Likewise, the metal component of the article under test corresponds to a particular type of connector, and the metal component of the reference article corresponds to the particular type of connector. As described above, the reference article includes a filler material between the metal component of the reference article and the carbon fiber composite component of the reference article. The filler material is configured to decrease an effective resistance of the reference article relative to the effective resistance of the article under test. The effective resistance of the article under test is indicative of a contact area between the carbon fiber composite component of the article under test and the metal component of the article under test.

The method 400 includes, at 402, comparing a temperature difference between the article under test and the reference article to a temperature criterion. For example, the temperature controller 152 may determine, based on the temperature indications 154, 156 from the temperature sensors 123, 133, whether the temperature difference satisfies the temperature criterion.

The method 400 includes, at 404, determining whether the temperature difference satisfies the temperature criterion. Based on a determination, at 404, that the temperature difference fails to satisfy the temperature criterion, the method 400 includes, at 406, adjusting a temperature of the article under test, a temperature of the reference article, or both. For example, based on a determination that the temperature difference fails to satisfy the temperature criterion, the method 400 may include applying heat to the article under test or to the reference article using a heating device of the non-destructive testing system 100. As another example, based on a determination that the temperature difference fails to satisfy the temperature criterion, the method 400 may include removing heat from the article under test or from the reference article using a cooling device of the non-destructive testing system 100.

Based on a determination, at 404, that the temperature difference satisfies the temperature criterion, the method 400 includes, at 408, sensing a thermoelectrically induced voltage between the article under test and the reference article, and at 410, sensing a thermoelectrically induced current between the article under test and the reference article. For example, the sensor(s) 142 may provide the signal(s) 144 to the processor 146. The signals 144 may include or represent data indicating a value of the thermoelectrically induced voltage and a value of the thermoelectrically induced current.

The method 400 may also include, at 412, generating, by the non-destructive testing system based on the thermoelectrically induced voltage and the thermoelectrically induced current, an output indicative of an effective resistance of the article under test. For example, the processor 146 may provide the output 182 to the output device 180.

The method 400 also includes, at 414, accessing lightning test data for articles subjected to a destructive lightning strike test. For example, the processor 146 may access the memory 170 to access the lightning test data 172. The lightning test data 172 may indicate or may be used, by the processor 146, to determine a relationship between the effective resistance of an article tested (or the contact surface of the article) and whether the article passed the lightning strike test.

The method 400 also includes, at 416, performing a comparison of value determined based on the thermoelectrically induced voltage and the thermoelectrically induced current to the lightning test data. For example, an effective resistance of the circuit 140 or of the article under test 101 may be compared to effective resistance data for the articles subjected to the destructive lightning strike test. As another example, the contact area 107 of the article under test 101 may be compared to contact areas of the articles subjected to the destructive lightning strike test. The method 400 also includes, at 418, generating, based on the comparison, an output indicating whether the article under test is expected to pass the destructive lightning strike test (e.g., to satisfying a lightning test standard).

Figure 5:
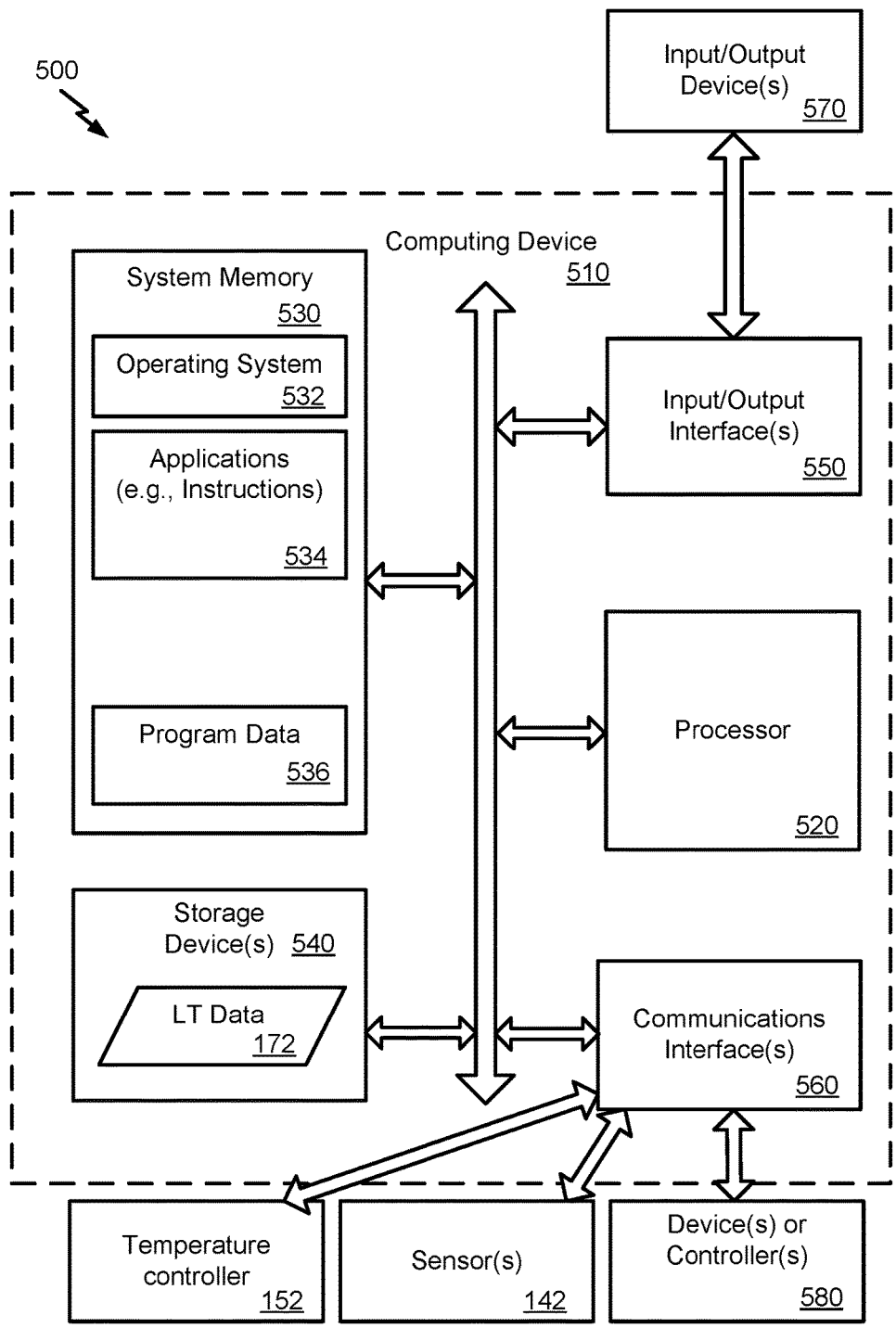
FIG. 5 is a block diagram of a particular example of a computing environment configured to support non-destructive testing according to the present disclosure.

FIG. 5 is an illustration of a block diagram of a computing environment 500 including a general purpose computing device 510 configured to support embodiments of computer-implemented methods and computer-executable program instructions (or code) according to the present disclosure. For example, the computing device 510, or portions thereof, may execute instructions to perform the functions of the non-destructive testing system 100 or functions of a portion of the non-destructive testing system 100, such as the processor 146 or the temperature controller 152. The instructions to control the non-destructive testing system 100 (or of a portion of the non-destructive testing system 100, such as the processor 146 or the temperature controller 152) may include instructions to determine whether a temperature difference between an article under test and a reference article satisfies a temperature criterion. The instructions to control the non-destructive testing system 100 (or the portion of the non-destructive testing system 100) may also include instructions to, based on a determination that the temperature difference satisfies the temperature criterion, sense a thermoelectrically induced voltage between the article under test and the reference article. The instructions to control the non-destructive testing system 100 (or the portion of the non-destructive testing system 100) may further include instructions to, based on a determination that the temperature difference satisfies the temperature criterion, sense a thermoelectrically induced current between the article under test and the reference article. The instructions to control the non-destructive testing system 100 (or the portion of the non-destructive testing system 100) may also include instructions to generate, based on the thermoelectrically induced voltage and the thermoelectrically induced current, an output indicating whether the article under test is expected to pass a destructive lightning strike test. The computing device 510, or portions thereof, may further execute instructions according to any of the methods described herein, such as the method 300 of FIG. 3 or the method 400 of FIG. 4.

The computing device 510 may include a processor 520. The processor 520 may communicate with the system memory 530, one or more storage devices 540, one or more input/output interfaces 550, one or more communications interfaces 560, or a combination thereof. In a particular embodiment, the processor 520 includes or corresponds to the processor 146 or the temperature controller 152. The system memory 530 may include volatile memory devices (e.g., random access memory (RAM) devices), nonvolatile memory devices (e.g., read-only memory (ROM) devices, programmable read-only memory, and flash memory), or both. The system memory 530 may include an operating system 532, which may include a basic/input output system for booting the computing device 510 as well as a full operating system to enable the computing device 510 to interact with users, other programs, and other devices. The system memory 530 may include one or more applications 534 which may be executable by the processor 520. For example, the one or more applications 534 may include instructions executable by the processor 520 to control the non-destructive testing system 100 to generate the output 182 indicating the effective resistance of the article under test 101, to generate the output 184 indicating whether the article under test 101 is likely to pass a destructive lightning strike test, such as a lightning direct effect test, or both.

The processor 520 may also communicate with one or more storage devices 540, such as the memory 170 of FIGS. 1 and 2. For example, the one or more storage devices 540 may include nonvolatile storage devices, such as magnetic disks, optical disks, or flash memory devices. The storage devices 540 may include both removable and non-removable memory devices. The storage devices 540 may be configured to store an operating system, images of operating systems, applications, and program data. The storage devices 540 may also store the lightning test (LT) data 172. In a particular embodiment, the memory 530, the storage devices 540, or both, include tangible computer-readable media.

The processor 520 may communicate with one or more input/output interfaces 550 that enable the computing device 510 to communicate with one or more input/output devices 570 (such as the output device 180 of FIGS. 1 and 2) to facilitate user interaction. The input/output interfaces 550 may include serial interfaces (e.g., universal serial bus (USB) interfaces or Institute of Electrical and Electronics Engineers (IEEE) 1394 interfaces), parallel interfaces, display adapters, audio adapters, and other interfaces. The input/output devices 570 may include keyboards, pointing devices, displays, speakers, microphones, touch screens, and other devices. The processor 520 may detect interaction events based on user input received via the input/output interfaces 550. Additionally, the processor 520 may send a display to a display device (e.g., the output device 180) via the input/output interfaces 550.

The processor 520 may communicate with the sensor(s) 142, the temperature controller 152, one or more devices 580, or a combination thereof, via the one or more communications interfaces 560. The one or more communications interfaces 560 may include wired Ethernet interfaces, IEEE 802 wireless interfaces, other wireless communication interfaces, or other network interfaces. The one or more devices 580 may include host computers, servers, workstations, and other computing devices.

The illustrations of the embodiments described herein are intended to provide a general understanding of the structure of the various embodiments. The illustrations are not intended to serve as a complete description of all of the elements and features of apparatus and systems that utilize the structures or methods described herein. Many other embodiments may be apparent to those of skill in the art upon reviewing the disclosure. Other embodiments may be utilized and derived from the disclosure, such that structural and logical substitutions and changes may be made without departing from the scope of the disclosure. For example, method steps may be performed in a different order than is shown in the figures or one or more method steps may be omitted. Accordingly, the disclosure and the figures are to be regarded as illustrative rather than restrictive.

Moreover, although specific embodiments have been illustrated and described herein, it should be appreciated that any subsequent arrangement designed to achieve the same or similar results may be substituted for the specific embodiments shown. This disclosure is intended to cover any and all subsequent adaptations or variations of various embodiments. Combinations of the above embodiments, and other embodiments not specifically described herein, will be apparent to those of skill in the art upon reviewing the description.

The Abstract of the Disclosure is submitted with the understanding that it will not be used to interpret or limit the scope or meaning of the claims. In addition, in the foregoing Detailed Description, various features may be grouped together or described in a single embodiment for the purpose of streamlining the disclosure. This disclosure is not to be interpreted as reflecting an intention that the claimed embodiments require more features than are expressly recited in each claim. Rather, as the following claims reflect, the claimed subject matter may be directed to less than all of the features of any of the disclosed embodiments.

What is claimed is:

1. A non-destructive testing system comprising:
   a test article interface comprising:
      a first electrical connector configured to couple to a metal component of an article under test; and
      a second electrical connector configured to couple to a carbon fiber composite component of the article under test;

a reference article interface comprising:
  a third electrical connector configured to couple to a metal component of a reference article; and
  a fourth electrical connector configured to couple to a carbon fiber composite component of the reference article;
at least one sensor electrically connected to the test article interface and electrically connected to the reference article interface and configured to generate at least one signal, the at least one signal based on a voltage between the test article interface and the reference article interface and based on a current between the test article interface and the reference article interface, the current and the voltage based on a temperature difference between the article under test and the reference article; and
a processor configured to generate, based on the at least one signal from the at least one sensor, an output indicating whether the article under test is expected to pass a lightning strike test.

2. The non-destructive testing system of claim 1, further comprising a temperature control system configured to control the temperature difference between the article under test and the reference article.

3. The non-destructive testing system of claim 2, wherein the temperature control system includes:
  a temperature controller;
  a first temperature sensor coupled to the test article interface and coupled to the temperature controller;
  a second temperature sensor coupled to the reference article interface and coupled to the temperature controller; and
  at least one heat transfer element coupled to the temperature controller,
  wherein the temperature controller is configured to receive a first temperature indication from the first temperature sensor, to receive a second temperature indication from the second temperature sensor, and to provide a control signal to the at least one heat transfer element to control the temperature difference between the article under test and the reference article, the control signal based the first temperature indication and the second temperature indication.

4. The non-destructive testing system of claim 3, wherein the at least one heat transfer element includes at least one heating device coupled to the test article interface and at least one cooling device coupled to the reference article interface.

5. The non-destructive testing system of claim 3, wherein the at least one heat transfer element includes at least one cooling device coupled to the test article interface and at least one heating device coupled to the reference article interface.

6. The non-destructive testing system of claim 1, wherein the processor is further configured to determine an effective resistance of the article under test and to perform a comparison of the effective resistance to lightning test data for articles subjected to a destructive lightning strike test, and wherein the output indicating whether the article under test is expected to pass the destructive lightning strike test is based on the comparison.

7. The non-destructive testing system of claim 1, wherein the carbon fiber composite component of the article under test and the carbon fiber composite component of the reference article are formed of a same type of composite material, and wherein the metal component of the article under test and the metal component of the reference article are a same type of connector.

8. The non-destructive testing system of claim 7, wherein the reference article further comprises a filler material between the metal component of the reference article and the carbon fiber composite component of the reference article, the filler material configured to decrease an effective resistance of the reference article relative to an effective resistance of the article under test.

9. The non-destructive testing system of claim 1, wherein the processor is further configured to determine a contact area of the article under test and to perform a comparison of the contact area to lightning test data for articles subjected to a destructive lightning strike test, and wherein the output indicating whether the article under test is expected to pass the destructive lightning strike test is based on the comparison.

10. The non-destructive testing system of claim 1, wherein the voltage and the current are induced by the temperature difference and thermoelectric properties of materials of the article under test and the reference article.

11. The non-destructive testing system of claim 1, wherein the test article interface and the reference article interface are electrically interconnected to form a circuit, the circuit electrically connecting a first portion of the article under test and a second portion of the reference article and electrically connecting the at least one sensor to a third portion of the article under test and to a fourth portion of the reference article.

12. A method comprising:
  determining, at a non-destructive testing system, whether a temperature difference between an article under test and a reference article satisfies a temperature criterion, the article under test comprising a carbon fiber composite component and a metal component;
  based on a determination that the temperature difference satisfies the temperature criterion:
    sensing, by the non-destructive testing system, a thermoelectrically induced voltage between the article under test and the reference article; and
    sensing, by the non-destructive testing system, a thermoelectrically induced current between the article under test and the reference article; and
  generating, by the non-destructive testing system based on the thermoelectrically induced voltage and the thermoelectrically induced current, an output indicating whether the article under test is expected to pass a lightning strike test.

13. The method of claim 12, further comprising, based on a determination that the temperature difference fails to satisfy the temperature criterion, adjusting, by the non-destructive testing system, a temperature of the article under test, a temperature of the reference article, or both.

14. The method of claim 12, further comprising, based on a determination that the temperature difference fails to satisfy the temperature criterion, applying heat to the article under test or to the reference article using a heating device of the non-destructive testing system.

15. The method of claim 12, further comprising, based on a determination that the temperature difference fails to satisfy the temperature criterion, removing heat from the article under test or from the reference article using a cooling device of the non-destructive testing system.

16. The method of claim 12, further comprising:
  accessing lightning test data for articles subjected to a destructive lightning strike test; and performing a comparison of a value, determined based on the thermoelectrically induced voltage and the thermoelectrically induced current, to the lightning test data; and wherein the output indicating whether the article under test is expected to pass the destructive lightning strike test is determined based on the comparison.

17. The method of claim 16, wherein the value includes an effective resistance of the article under test, an effective resistance of a circuit including the article under test, a contact area between the carbon fiber composite component of the article under test and the metal component of the article under test, or a combination thereof.

18. The method of claim 12, wherein the carbon fiber composite component of the article under test is formed of a particular composite material and the reference article includes a carbon fiber composite component formed of the particular composite material, wherein the metal component of the article under test corresponds to a particular type of connector and the reference article includes a metal component that corresponds to the particular type of connector, and wherein the reference article further comprises a filler material between the metal component of the reference article and the carbon fiber composite component of the reference article, the filler material configured to decrease an effective resistance of the reference article relative to an effective resistance of the article under test.

19. A non-transitory computer readable storage device storing instructions that, when executed by a processor of a non-destructive testing system, cause the processor of the non-destructive testing system to perform operations comprising:

determining whether a temperature difference between an article under test and a reference article satisfies a temperature criterion;

based on a determination that the temperature difference satisfies the temperature criterion, determining an effective resistance of the article under test based on a thermoelectrically induced voltage between the article under test and the reference article and based on a thermoelectrically induced current between the article under test and the reference article; and generating an output indicating whether the article under test is expected to pass a lightning strike test.

20. The non-transitory computer readable storage device of claim 19, wherein the operations further comprise:

performing a comparison of a value, determined based on the thermoelectrically induced voltage and the thermoelectrically induced current, to lightning test data for articles subjected to a destructive lightning strike test, wherein the output is determined based on the comparison.

* * * * *